US008800158B1

(12) United States Patent
Shim

(10) Patent No.: US 8,800,158 B1
(45) Date of Patent: Aug. 12, 2014

(54) APPARATUS FOR CUTTING AND FABRICATING ALLOGRAFTS

(71) Applicant: John H. Shim, Tampa, FL (US)

(72) Inventor: John H. Shim, Tampa, FL (US)

( * ) Notice: Subject to any disclaimer, the term of this patent is extended or adjusted under 35 U.S.C. 154(b) by 0 days.

(21) Appl. No.: 14/254,430

(22) Filed: Apr. 16, 2014

Related U.S. Application Data

(60) Provisional application No. 61/838,594, filed on Jun. 24, 2013.

(51) Int. Cl.
*A61B 17/56* (2006.01)
*A61B 17/16* (2006.01)

(52) U.S. Cl.
CPC .................................. *A61B 17/1635* (2013.01)
USPC ............................................. 33/630; 606/87

(58) Field of Classification Search
CPC ........ A61B 17/58; A61B 17/56; A61B 17/15; A61B 17/90; A61B 17/00; A61B 17/88
USPC ......................................... 33/630; 606/87, 88
See application file for complete search history.

(56) References Cited

U.S. PATENT DOCUMENTS

| | | | |
|---|---|---|---|
| D355,254 S * | 2/1995 | Krafft et al. ................. D24/140 |
| D376,202 S * | 12/1996 | Burke et al. ................. D24/140 |
| 5,722,978 A * | 3/1998 | Jenkins, Jr. ..................... 606/87 |
| 5,897,559 A * | 4/1999 | Masini ........................ 606/86 R |
| 5,916,220 A * | 6/1999 | Masini ............................ 606/88 |
| 5,961,523 A * | 10/1999 | Masini ........................ 606/86 R |
| 6,102,916 A * | 8/2000 | Masini ............................ 606/88 |
| 6,500,179 B1 * | 12/2002 | Masini ............................ 606/88 |
| 6,648,894 B2 | 11/2003 | Abdelgany et al. |
| 6,962,592 B2 | 11/2005 | Gatturna et al. |
| 7,104,997 B2 * | 9/2006 | Lionberger et al. ............. 606/88 |
| 7,364,581 B2 * | 4/2008 | Michalowicz .................. 606/87 |
| 7,621,919 B2 * | 11/2009 | Williams et al. ................ 606/87 |
| 7,699,851 B2 | 4/2010 | Dalton |
| 7,727,238 B2 * | 6/2010 | Seo et al. ........................ 606/88 |
| 7,736,366 B2 | 6/2010 | Abdelgany et al. |
| 7,736,367 B2 * | 6/2010 | Kuczynski ................. 606/86 R |
| 7,780,672 B2 * | 8/2010 | Metzger et al. ................. 606/88 |
| 7,802,503 B2 | 9/2010 | Couvillion et al. |
| 8,052,692 B2 * | 11/2011 | Lionberger et al. ............. 606/88 |
| 8,127,646 B2 | 3/2012 | Couvillion et al. |
| 8,197,486 B2 * | 6/2012 | Oti et al. ......................... 606/87 |
| 2002/0082604 A1 * | 6/2002 | Abdelgany et al. ............. 606/79 |
| 2004/0034362 A1 * | 2/2004 | Abdelgany et al. ............. 606/98 |
| 2005/0154394 A1 * | 7/2005 | Michalowicz .................. 606/87 |
| 2005/0273113 A1 * | 12/2005 | Kuczynski ...................... 606/88 |
| 2006/0217732 A1 * | 9/2006 | Seo et al. ........................ 606/87 |
| 2008/0015602 A1 * | 1/2008 | Axelson ......................... 606/87 |
| 2008/0275452 A1 * | 11/2008 | Lang et al. ...................... 606/88 |
| 2013/0296871 A1 * | 11/2013 | Lazar et al. ..................... 606/87 |

* cited by examiner

*Primary Examiner* — Yaritza Guadalupe-McCall

(74) *Attorney, Agent, or Firm* — Nilay J. Choksi; Smith & Hopen, P.A.

(57) ABSTRACT

An apparatus for the accurate and efficient fabrication of individualized cortical allograft bone implants from graft material, such as cortical struts, in particular as used in cervical and lumbar allografts. The apparatus includes a base and an overhanging hood affixed to the base with a channel running therethrough, where the channel has an irregular shape defined by the graft material used for fabricating the resulting allografts. The hood further includes a plurality of vertical and horizontal cutting guides that are specifically angled based on the allografts needed. Graft material is inserted into the channel between the base and hood, and a blade or other medical instrument is inserted into the cutting guides for cutting and fabricating the allograft from the graft material.

20 Claims, 5 Drawing Sheets

APPARATUS FOR CUTTING AND FABRICATING ALLOGRAFTS

CROSS-REFERENCE TO RELATED APPLICATIONS

This nonprovisional application is a continuation of and claims priority to provisional application No. 61/838,594, entitled "Apparatus and Method for Cutting and Fabricating Cortical Bone Grafts", filed Jun. 24, 2013 by the same inventor, the entirety of which is incorporated herein by reference.

BACKGROUND OF THE INVENTION

1. Field of the Invention

This invention relates, generally, to allografts. More specifically, it relates to an apparatus and method for fabricating bone grafts from cortical segments.

2. Brief Description of the Prior Art

The procedure of allotransplantation is known in the art for effectively transplanting tissue from one individual (donor) to another individual (recipient) of the same species. In particular, bone grafts are used to replace or enhance bones of individuals whose own bones have degenerated or have become damaged through injury. Further, cortical and lumbar allografts are often used in spinal fusions, or other orthopedic procedures for the replacement of bone tissue.

Often, cortical allografts are utilized in the cervical region of a spine (i.e., during cervical spinal fusions, corpectomies, etc.), and lumbar allografts are utilized in the lumbar region of the spine (i.e., lumbar spinal fusions, corpectomies, etc.). However, each cortical allograft ring or wedge is quite costly (well over $1,000 per ring or wedge used per level on a single patient with a patient potentially having as many as four (4) levels performed during a surgery), and as such, that cost is typically passed on to the patient. Different types of pre-cut cortical allograft rings or wedges are needed by different patients and are thus purchased by the healthcare institutions based on needs of the patients.

Healthcare institutions have attempted to lower this cost by purchasing cortical struts or segments that can be manually cut to create the appropriately sized rings or wedges. Cutting these cortical struts typically involves various hand instruments, such as bone-cutting shears/scissors, osteotomes, bone-cutting saw blades and the like. However, manually forming these bone grafts from cortical struts is very time-consuming and requires significant effort before or during a surgical procedure where time and money are important commodities.

Tabletop apparatuses used fir cutting and fabricating bone grafts are known in the art, though each has its own limitations or drawbacks that are overcome by the current invention. For example, U.S. Pat. Nos. 6,648,894 and 7,736,366 to Abdelgany et al. describe an apparatus and method for guiding and forming a bone graft. The apparatus/guide includes a holding mechanism to hold the graft material in place and a pattern that corresponds to the pattern desired for the shape of the bone graft. The guide can further include a cutting guide with a pattern desired for the shape of the bone graft. However, utilizing this apparatus and the methodology taught therein, a surgical team would need to expend an excess amount of time and effort forming a single bone graft, where time and effort are very important considerations for overall cost and time of the surgical procedure.

U.S. Pat. No. 6,962,592 to Gatturna et al. describes an apparatus for cutting allograft bone implants from donor bone. The donor bone is placed on a flat surface, and pneumatic cylinders with blades are lowered to cut the bone in order to form allograft bone implants. However, this apparatus requires several automated moving parts and would be difficult to manufacture and use. This requires excess time and effort to be expended by the surgical team, along with increased possibility of machine malfunction.

U.S. Pat. No. 7,699,851 to Dalton relates to a bone cutting jig system for spinal implant procedures. The system requires two separate cutting jigs. In the first cutting jig, two cutting guides are disposed in bi-convex configuration, and the surgical team must operate a uniquely designed reciprocating saw against the cutting guides to cut the graft material. This would require excess time and energy to be expended by the surgical team, along with an additional skill needed by the surgical team to make the appropriate cuts. Additionally, the biconvex configuration of the cutting guides would fail to product bone grafts suitable for cervical allotransplantation.

U.S. Pat. No. 7,802,503 to Couvillion et al relates to an apparatus for preparing bone grafts, in particular grafts for lumbar/thoracic interbody fusion. The apparatus includes a bone holder connected to an arm that is hingedly coupled to one end of a base. On the other end of the base is a serrated surface. When a bone graft is to be cut, the bone holder hinges toward the base and serrated surface holding the bone against the serrated edge. The bone holder includes two cutting guides through which the surgical team must insert blades to cut and form the bone graft. This technology suffers from a few of the same issues seen in the '851 patent. The blades are not conducive for forming cervical allografts, and the apparatus requires an excess amount of manual effort and time to be expended. There are also many moving parts that can hinder the overall effectiveness and efficiency of the apparatus.

U.S. Pat. No. 8,127,646 to Couvillion et al. describes an apparatus for preparing bone grafts, in particular grafts for cervical interbody fusion, though quite similar to the '503 patent. The apparatus includes a bone holder connected to an arm that can be secured to one end of a base. On the other end of the base are a plurality of fingers. When a bone graft is to be cut, the bone holder is secured to the base such that the bone is held against the fingers. The bone holder includes its own set of fingers with a plurality of slots therebetween that line up with the fingers on the base. The slots in the bone holder are a guide as to where the surgical team would insert blades to cut and form the bone graft. Though this technology is intended to form cervical bone grafts, it suffers from similar issues to that seen in the '503 patent in that it requires an excess amount of manual effort and time to be expended.

Accordingly, what is needed is an apparatus that facilitates the efficient and accurate fabrication of cortical rings or wedges, in particular for cervical allotransplantation. However, in view of the art considered as a whole at the time the present invention was made, it was not obvious to those of ordinary skill in the field of this invention how the shortcomings of the prior art could be overcome.

All referenced patents are incorporated herein by reference in their entireties. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an integrated (i.e., minimal moving parts) and more efficient apparatus for cutting and fabricating allografts is now met by a new, useful, and nonobvious invention.

In an embodiment, the current invention is an apparatus for cutting graft material and fabricating an allograft therefrom. The apparatus includes a base that defines the front, rear, left, right, top, and bottom of the apparatus. The base has a lead portion and a trail portion, where the lead portion has an entry end and the trail portion has an exit end. The entry and exit ends are about the same size. The apparatus further includes a hood coupled to the base and positioned in overlying relation to the base. The hood has a top portion, rear portion, and front portion. A channel is disposed between the base and the hood, where the channel is positioned in overlying relation to the base and in underlying relation to the hood. The channel has an irregular shape to help secure the graft material therewithin. The channel further has a first end in communication with the entry end of the base and a second end in communication with the exit end of the base. The channel is spatially confined on its bottom, top, and rear by the base and the hood. The apparatus further includes a first vertical cutting guide and a second vertical cutting guide each disposed through the top portion of the hood near the second/exit end of the hood and adjacent to each other. The cutting guides provide open communication between the top of the apparatus and an interior of the channel through each cutting guide. Each is structured to receive a blade without excessive spatial leeway, so that the blade can accurately cut the graft material from the top through the cutting guides. Each cutting guide is disposed at its own predetermined angle based on the shape of the allograft needed/desired.

The apparatus may further include a first and second horizontal cutting guide disposed through the rear portion of the hood near the second end of the hood and adjacent to each other. The horizontal cutting guides provide open communication between the rear of the apparatus and the interior of the channel through each horizontal cutting guide. Each is structured to receive a blade without excessive spatial leeway, so that the blade can accurately cut the graft material from the front or rear through the horizontal cutting guides. The first and second horizontal cutting guides are aligned with the first and second vertical cutting guides, respectively, and are disposed at the respective predetermined angles.

The apparatus may further include a first and second rear interruption between the first vertical cutting guide and the first horizontal cutting guide and between the second vertical cutting guide and the second horizontal cutting guide, respectively. The rear interruptions are generally solid so that the blade cannot pass freely between the vertical cutting guides and horizontal cutting guides through the rear interruptions.

The apparatus may further include a first and second front interruption disposed in the front portion of the hood in the first and second vertical cutting guides, respectively. The front interruptions are generally solid so that the vertical cutting guides are not in open communication with the front of the apparatus.

The predetermined angle of the first vertical cutting guide may be about three (3) degrees to about six (6) degrees, most preferably five (5) degrees, as is needed for fabrication of cervical and lumbar allograft wedges. The predetermined angle of the second vertical cutting guide may be vertically-oriented. The first vertical cutting guide would be angled or directed toward the second vertical cutting guide.

The apparatus may further include a first and second notch in the base aligned with the first and second vertical cutting guides, respectively. The first notch would be disposed at the angle of first vertical cutting guide, and the second notch would be disposed at the angle of the second vertical cutting guide.

The apparatus may further include a third vertical cutting guide disposed through the top portion of the hood adjacent to the first and second vertical cutting guides on an opposite side of the second vertical cutting guide from the first vertical cutting guide. The third cutting guide provides open communication between the top of the apparatus and an interior of the channel through that cutting guide. It is structured to receive a blade without excessive spatial leeway, so that the blade can accurately cut the graft material from the top through the third cutting guide. It is also disposed at its own predetermined angle based on the shape of the allograft needed/desired.

In a further embodiment, the apparatus may further include a first, second, and third horizontal cutting guide disposed through the rear portion of the hood near the second end of the hood and adjacent to each other. The horizontal cutting guides provide open communication between the rear of the apparatus and the interior of the channel through each horizontal cutting guide. Each is structured to receive a blade without excessive spatial leeway, so that the blade can accurately cut the graft material from the front or rear through the horizontal cutting guides. The first, second, and third horizontal cutting guides are aligned with the first, second, and third vertical cutting guides, respectively, and are disposed at the respective predetermined angles. In yet a further embodiment, the apparatus may further include a first, second, and third rear interruption between the first vertical cutting guide and the first horizontal cutting guide, between the second vertical cutting guide and the second horizontal cutting guide, and between the third vertical cutting guide and the third horizontal cutting guide, respectively. The rear interruptions are generally solid so that the blade cannot pass freely between the vertical cutting guides and horizontal cutting guides through the rear interruptions.

In another embodiment with the third vertical cutting guide, the apparatus may further include a first, second, and third front interruption disposed in the front portion of the hood in the first, second, and third vertical cutting guides, respectively. The front interruptions are generally solid so that the vertical cutting guides are not in open communication with the front of the apparatus.

In yet another embodiment with the third vertical cutting guide, the predetermined angle of the first and third vertical cutting guides may be about three (3) degrees to about six (6) degrees, most preferably five (5) degrees, as is needed for fabrication of cervical and lumbar allograft wedges. The predetermined angle of the second vertical cutting guide may be vertically-oriented. The first and third vertical cutting guides would be angled or directed in opposite directions but each toward the second vertical cutting guide.

In still another embodiment with the third vertical cutting guide, the apparatus may further include a first, second, and third notch in the base aligned with the first, second, and third vertical cutting guides, respectively. The first notch would be disposed at the angle of first vertical cutting guide, the second notch would be disposed at the angle of the second vertical cutting guide, and the third notch would be disposed at the angle of the third vertical cutting guide.

The base may include support flanges extending to the front of the apparatus and to the rear of the apparatus for stability of the apparatus during use.

The base may include a gap disposed between the hood and the base along the front of the apparatus, such that the interior of the channel is in open communication with the front of the apparatus.

The irregular shape of the channel may include a first surface that substantially horizontal and forms the bottom side of the channel, a second surface extending rearwardly and upwardly from the first surface, a first joint that connects the first and second surfaces, a third surface extending frontwardly and upwardly from the second surface, and a second joint that connects the second surface and the third surface. In a further embodiment, the irregular shape can also include a fourth surface that is substantially horizontal and extends frontwardly from the third surface and a third joint that connects the third and fourth surfaces. In this way, the fourth surface would form the top side of the channel and be disposed parallel to and in overlying relation to the first surface.

In a separate embodiment, the current invention is an apparatus for cutting cortical struts and fabricating a cervical or lumbar allograft therefrom, where the apparatus can include each and every one of the foregoing limitations or features in a single embodiment.

In another embodiment, the current invention is an apparatus for cutting graft material and fabricating an allograft therefrom. The apparatus includes a base that defines the front, rear, left, right, top, and bottom of the apparatus. The base has a lead portion and a trail portion, where the lead portion has an entry end and the trail portion has an exit end. The entry and exit ends are about the same size. The apparatus further includes a hood coupled to the base and positioned in overlying relation to the base. The hood has a top portion, rear portion, and front portion. A channel is disposed between the base and the hood, where the channel is positioned in overlying relation to the base and in underlying relation to the hood. The channel has an irregular shape to help secure the graft material therewithin. The channel further has a first end in communication with the entry end of the base and a second end in communication with the exit end of the base. The channel is spatially confined on its bottom, top, and rear by the base and the hood. The apparatus further includes a first horizontal cutting guide and a second horizontal cutting guide each disposed through the rear portion of the hood near the second/exit end of the hood and adjacent to each other. The cutting guides provide open communication between the rear of the apparatus and an interior of the channel through each cutting guide. Each is structured to receive a blade without excessive spatial leeway, so that the blade can accurately cut the graft material from the front or rear through the cutting guides. Each cutting guide is disposed at its own predetermined angle based on the shape of the allograft needed/desired.

These and other important Objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
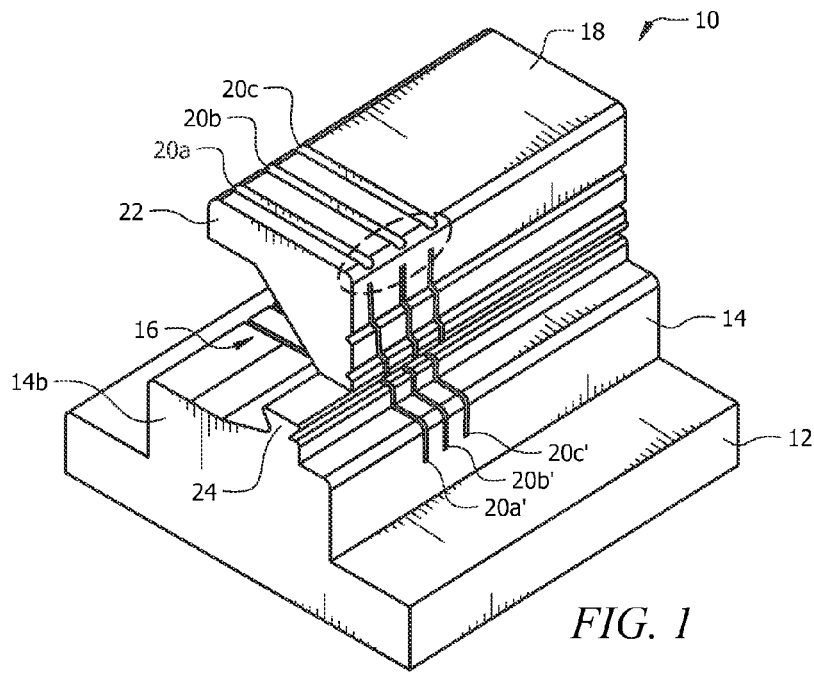
FIG. 1 is a rear perspective view of an embodiment of the current invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

In an embodiment, the current invention is an apparatus for the accurate and efficient fabrication of individualized cortical allograft bone implants from cortical struts (e.g., radius and fibula struts), in particular as used in cervical allografts, lumbar allografts and polyetheretherketone (PEEK) cages. The apparatus is shown from different angles in FIGS. 1-7 and is generally denoted by the reference numeral 10. Apparatus 10 generally has any suitable, depending on use (e.g., cervical allograft versus lumbar allograft, etc.), for example three (3) inches, which might typically be used to fabricate cervical allografts.

Figure 5:
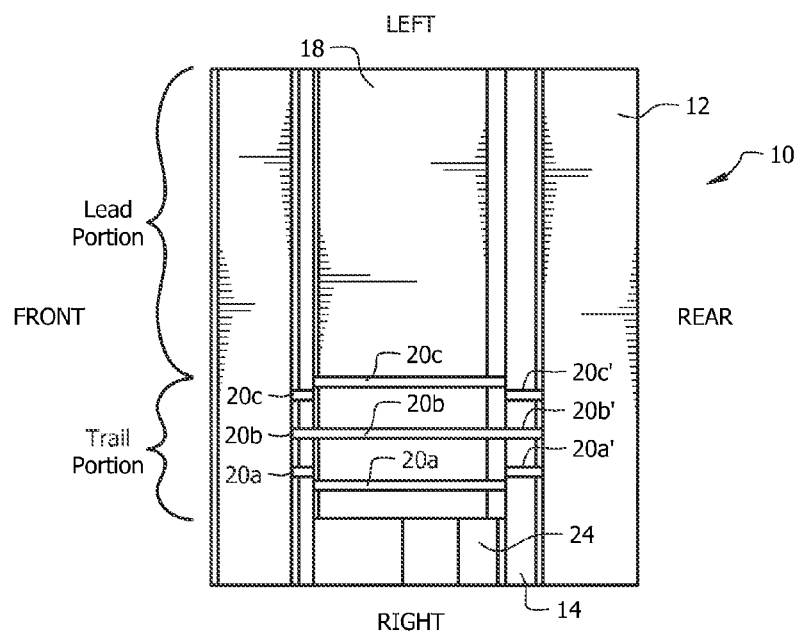
FIG. 5 is a top view of an embodiment of the current invention.

Apparatus 10 includes a generally planar support, referred to by the reference numeral 12, having a surface that defines the horizontal and vertical axes of apparatus 10, though it should be understood that various embodiments of the invention can be utilized at different angles and in different positions. Support 12 further defines the front, rear, left side, and right side of apparatus 10, as can be seen in FIG. 5. Support 12 can provide additional stability to apparatus 10 during cutting of the cortical strut via the support flanges that extend past the front and rear of base 14.

As noted, apparatus 10 further includes a base, generally denoted by the reference numeral 14, positioned in overlying relation to support 12. Base 14 typically has similar or smaller dimensions than support 12, in part due to the support flanges extending from support 12. Base 14 has a longitudinal extent with first end 14a and second end 14b. Hood 18 has a first end that is proximal to first end 14a of base 14 and a second end that is proximal to second end 14b of base 14. The second end of hood 18 includes cutting area 22 proximal to second end 14b of base 14.

Channel 16 is formed within the interior spatial confines of base 14 and hood 18, as will become apparent as this specification continues. Base 14 has a horizontal line of axis along which including a lead portion where the first end of hood 18 is positioned and a trail portion where cutting guides 20a, 20b, 20c are disposed. This can be best seen in FIGS. 1-6, in particular FIGS. 5 and 6.

The longitudinal extent of base 14 includes elongate channel 16 therethrough, as can be seen in FIGS. 1-4 and 6-7. Channel 16 is disposed along the entirety of the longitudinal extent of hood 18 in overlying relation to base 14. The first end of channel 16 is aligned with or positioned in proximity to first end 14a of base 14, and the second end of channel 16 is aligned with or positioned in proximity to second end 14b of base 14. Channel 16 is in open communication with the external environment in front of base 14 (to facilitate viewing of the graft material within channel 16) and on both sides of base 14 for entry and exit of the graft material into and out of channel 16.

Base 14 can include measurement indicators 26 on its top surface (i.e., bottom surface of channel 16) for a user's reference during cutting and fabrication of allografts from the graft material.

Figure 7:
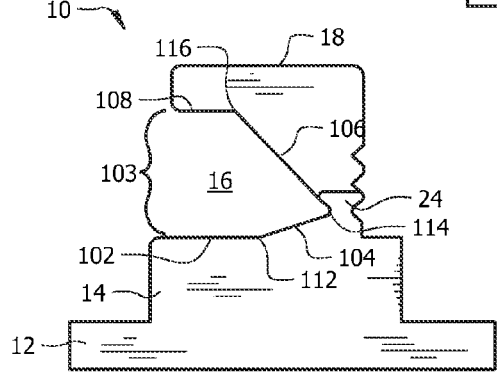
FIG. 7 is an end view of an embodiment of the current invention.

As seen in FIG. 7, channel 16 has an irregular shape that is defined by the bone or graft material (e.g., cortical strut) that is to be cut and broken down into bone allografts. In an embodiment as seen in FIGS. 1-4 and 7, channel 16 is structured to fit a cortical strut or the like for formation of allografts, typically cervical and lumbar allografts.

Figure 10:
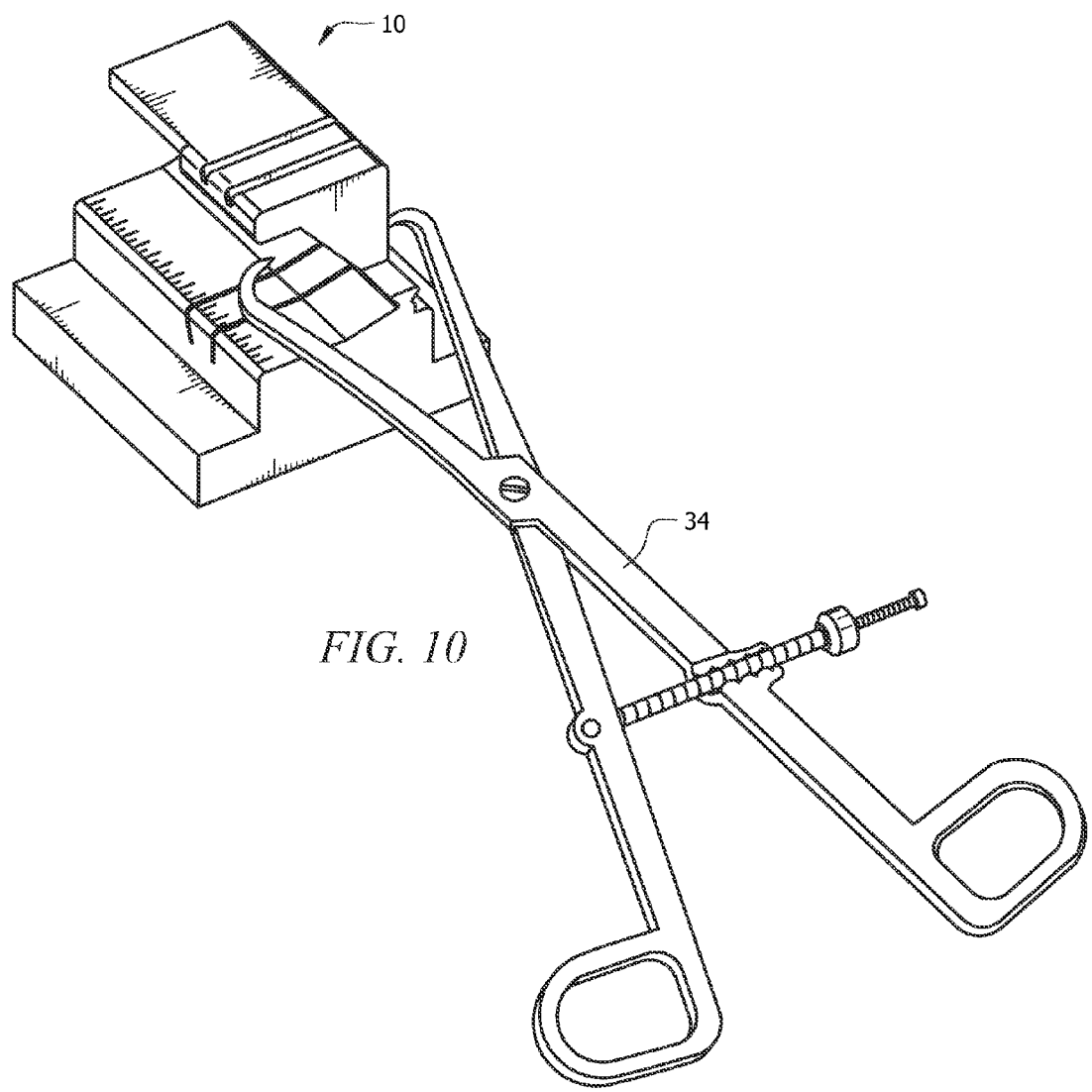
FIG. 10 depicts how a forceps can hold a cortical strut in place while being cut and/or fabricated within an embodiment of the current invention.

Channel 16 may be lined with a friction-enhancing material or polymer (not shown) that increases the friction between the walls of channel 16 and the graft material positioned therewithin. Another option is for the lining (whether on the friction-enhancing material or on the walk of channel 16) can be rough or otherwise patterned to further increase friction between the walls of channel 16 and the graft material positioned therewithin. Enhancing friction in these or other manners further secures the position of the graft material within channel 116, which in turn allows for more accurate positioning and cutting. It can be appreciated that other mechanisms of holding a graft material in place during cutting is contemplated by the current invention. An example can be seen in FIG. 10 where the graft material (cortical strut) would be held in place by using conventional forceps 34 to immobilize the graft material to apparatus 10.

Referring back to FIG. 7, channel 16 has an irregular shape that is defined by a cortical strut to be cut for cervical allografts. The irregular shape is utilized for optimal interference fit of the graft material and security of the graft material within the channel. This shape can be most clearly seen in FIG. 7 and has at least four (4) surfaces: first surface 102, second surface 104, third surface 106, and fourth surface 108. The four (4) surfaces are connected to one other via joints 112, 114, and 116.

First surface 102 is substantially horizontal/level and extends horizontally in position below hood 18, such that an optional gap, generally referred to by the reference numeral 103, can exist between first surface 102 and hood 18 as seen in FIG. 7. Gap 203 facilitates viewing of the cutting and fabrication of the allografts. First surface 102 is a substantially horizontal plane relative to the horizontal axis of support 12 (i.e., first surface 102 of channel 16 is parallel to the top surface of support 12).

In proximity to a vertical line of axis of base 114 (where the vertical line of axis would run vertically down the center of apparatus 10 seen in FIG. 7), second surface 104 is connected to first surface 102 at oblique (specifically, obtuse) joint 112. Second surface 10.4 is a plane that is rearwardly and upwardly slanted or angled relative to the plane of first surface 102.

The rearmost edge of second surface 104 leads into arcuate bend or elbow 114 that acutely bends and connects to third surface 106. Arcuate bend or elbow 114 is angled to fit the curvature or contour of the bone or graft material. In the case of cortical struts used for cervical and lumbar allografts, an acutely-angled elbow, as seen in FIG. 7 is typically needed.

Third surface 106 is a plane that is frontwardly and upwardly slanted or angled, of which the rear edge commences from arcuate elbow 114 and the front edge terminates at oblique (specifically obtuse) joint 116. The angle or slant of third surface 106 may be steeper than the angle or slant of second surface 104. Optionally, oblique joint 116 can be acute and lead to a fifth surface (not shown) that can secure the top part of the allograft material (cortical strut).

In FIG. 7, oblique joint 116 is the apex of channel 116 and plateaus into fourth surface 108, which can be level (i.e., parallel to first surface 102) and extend frontwardly from oblique joint 116 toward the front of apparatus 10.

Apparatus 10 further includes cutting area 22 in proximity to the second end of hood 18 (trail end of base 14). If hood 18 does not extend completely to second end 14b of base 14, as best seen in FIG. 3 (i.e., if cutting area 22 terminates prior to second end 14b of base 14), guiding flange 24 along the rear edge of base 1.4 can guide the graft material or resulting allograft out of channel 16 along base 14.

Figure 2:
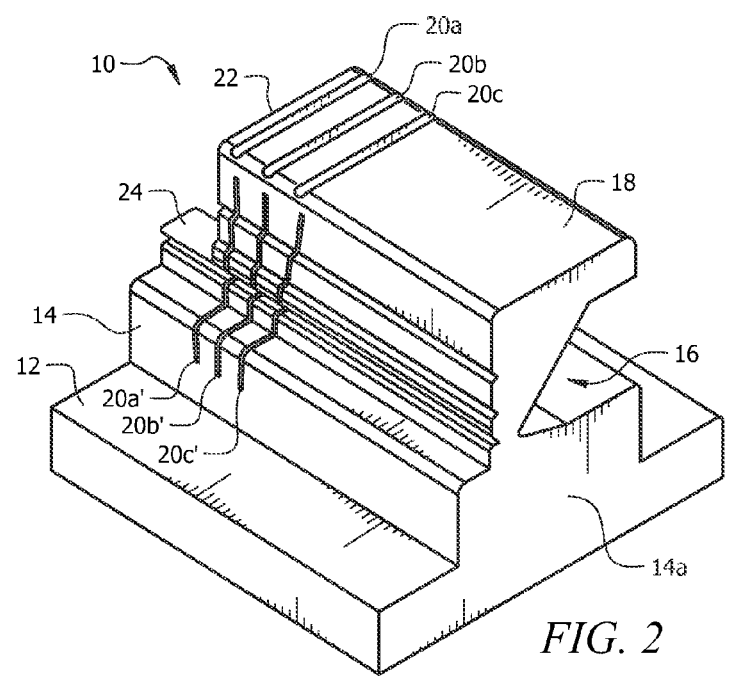
FIG. 2 is a rear perspective view of an embodiment of the current invention.
Figure 3:
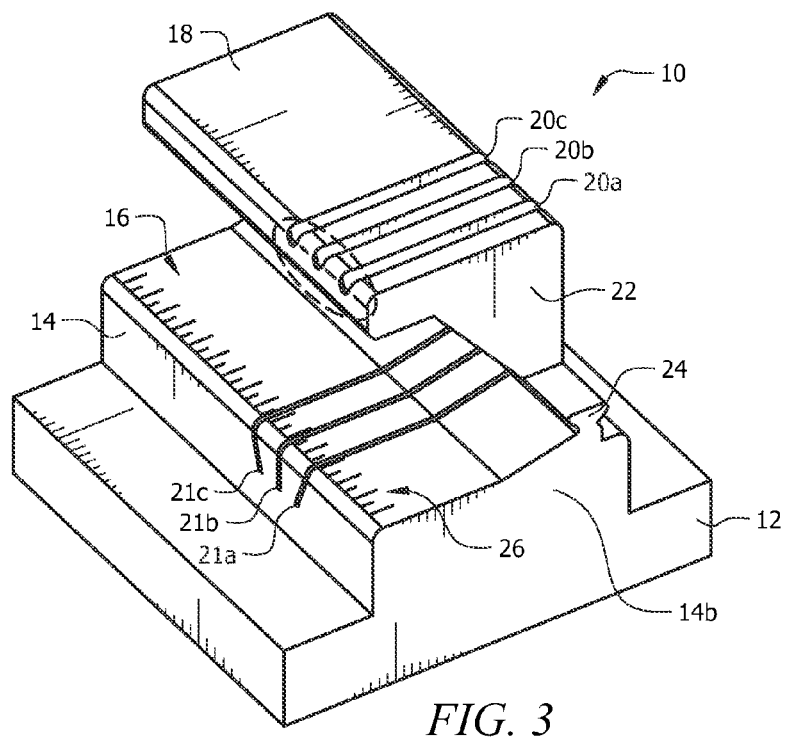
FIG. 3 is a front perspective view of an embodiment of the current invention.

Cutting area 22 includes a plurality of cutting guides 20a, 20b, 20c and typically has an inverted L-shape, substantially similar to the shape seen in hood 18 as indicated in FIGS. 1-3. As described previously, channel 16 continues through and within at least a portion of the trail portion of base 14.

Cutting guides 20a, 20b, 20c are structured to receive a blade or device for cutting the graft material positioned underneath cutting guides 20a, 20b, 20c. Cutting guides 20a, 20b, 20c may be structured or adjustable at any position or angle to accommodate particular needs for resulting allografts. As seen in FIGS. 1-7, cutting guides 20a, 20b, 20c are angled to fabricate cervical and lumbar allografts.

Figure 6:
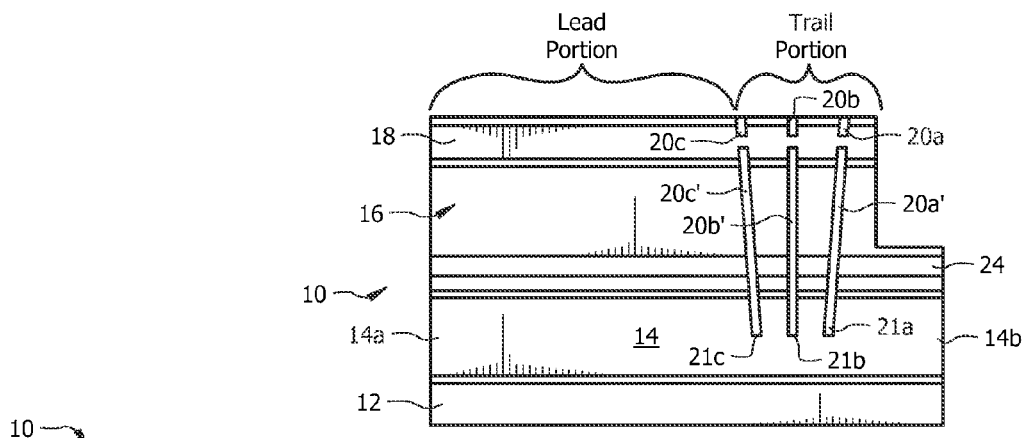
FIG. 6 is a front view of an embodiment of the current invention.

As can be seen most clearly in FIG. 6, cutting guide 20h is substantially vertical to facilitate a vertical cut through the bone or graft material. Cutting guides 20a and 20c have predetermined positions spaced away from cutting guide 20b and are structured to make an angled cut through the bone or graft material. When fabricating a cervical or lumbar allograft, cutting guides 20a and 20c each typically has a tilt or angle of about three (3) degrees to about six (6) degrees toward cutting guide 20b (e.g., for lordotic cuts), where the angle is relative to the vertical axis of base 14 or to the vertical axis of cutting guide 20b.

Figure 9:
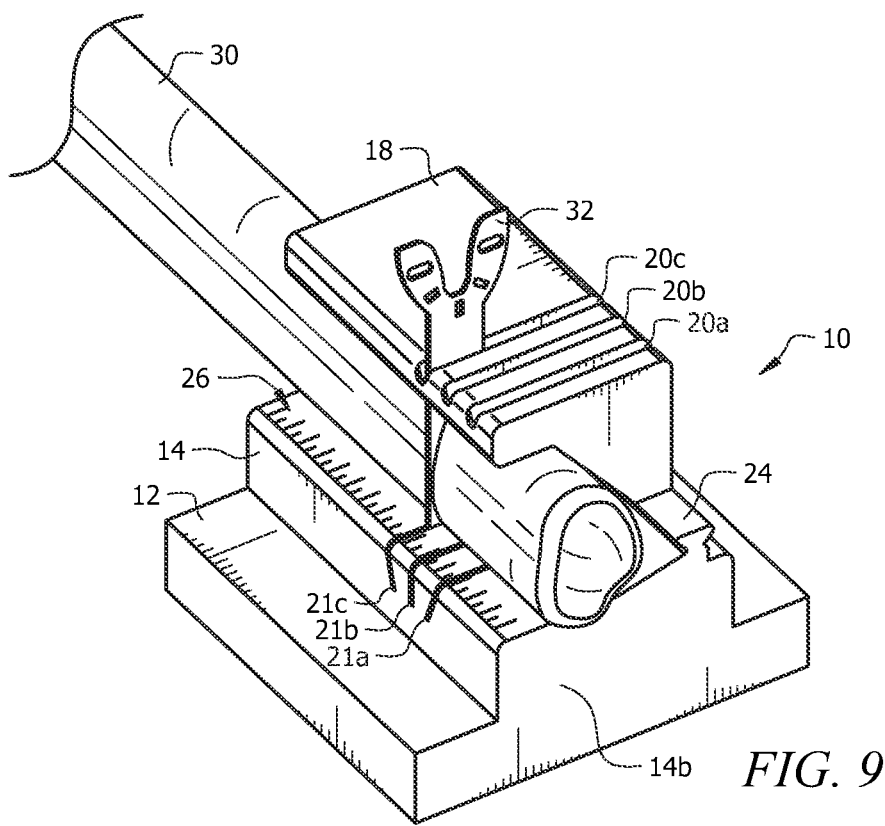
FIG. 9 shows the cortical strut of FIG. 8 in a position being cut by a saw blade.

As can be seen in FIGS. 1-3, hood 18 has a front portion, a top portion, and a rear portion. In proximity to cutting area 22, the top portion of hood 18 includes vertical cutting guides 20*a*, 20*b*, 20*c* that are disposed through the top portion of hood 18. Horizontal cutting guides 20*a'*, 20*b'*, 20*c'* are disposed through the rear portion of hood 18 and are vertically aligned with vertical cutting guides 20*a*, 20*b*, 20*c*, as can also be seen in FIGS. 5 and 6. As depicted in FIG. 5, horizontal cutting guides 20*a'*, 20*c'* may be offset from corresponding vertical cutting guides 20*a*, 20*c*, respectively, since vertical cutting guides 20*a*, 20*c* are slightly angled, as discussed. FIGS. 1 and 2 further show that horizontal cutting guides 20*a'*, 20*c'* can also be angled similar to vertical cutting guides 20*a*, 20*c*. Horizontal cutting guides 20*a'*, 20*b'* 20*c'* provides a user with the option to cut graft material from a horizontal orientation rather than from a vertical orientation through vertical cutting guides 20*a*, 20*b*, 20*c* (e.g., as seen in FIG. 9.).

As can be seen in FIGS. 1, 2, and 6, the corner between the top and rear portions of hood 18 can be solid, an interruption, or a break (broken circle in FIG. 1) between vertical cutting guides 20*a*, 20*b*, 20*c* and horizontal cutting guides 20*a'*, 20*b'*, 20*c'*, respectively. This break in cutting guides 20*a*-20*c*, 20*a'*-20*c'* can be provided for safety and efficiency of cuts. Because of these breaks, osteotome, saw blade, or other cutting apparatus 32 (FIG. 9) would be incapable of exiting out of the rear of apparatus 10.

Similarly, as can be seen in FIG. 3, the front portion of hood 18 can include a break (broken circle in FIG. 3) in vertical cutting guides 20*a*, 20*b*, 20*c*. This break in cutting guides 20*a*, 20*b*, 20*c* can also be provided for safety and efficiency of cuts. Because of these breaks, osteotome, saw blade, or other cutting apparatus 32 (FIG. 9) would be incapable of exiting out of the front of apparatus 10.

Further, the top surface of base 14 (i.e., the bottom surface of channel 16) can include notches 21*a*, 21*b*, 21*c* in direct underlying relation to cutting guides 20*a*, 20*b*, 20*c*, respectively. As depicted in FIG. 5, notches 21*a*, 21*c* may be offset from corresponding vertical cutting guides 20*a*, 20*c*, respectively, since vertical cutting guides 20*a*, 20*c* are slightly angled, as discussed. FIG. 6 further shows that notches 21*a*, 21*c* can also be angled similar to vertical cutting guides 20*a*, 20*c*. Notches 21*a*, 21*b*, 21*c* allow osteotome, saw blade, or other cutting apparatus 32 to cut through graft material 30 via vertical cutting guides 20*a*, 20*b*, 20*c* or horizontal cutting guides 21*a*, 21*b*, 21*c* through notches 21*a*, 21*b*, 21*c*.

Figure 4:
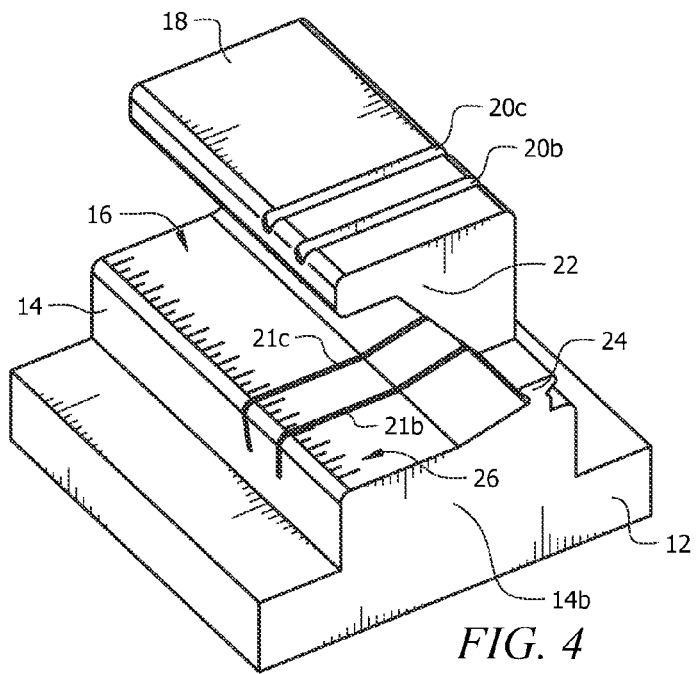
FIG. 4 is a front perspective view of an alternate embodiment of the current invention.

In an alternate embodiment, as seen in FIG. 4, cutting guides 20*b*, 20*c* are present in cutting area 22, and cutting guide 20*a* is absent from the embodiment. Cutting guide 20*a* can optionally be added, as in previously described embodiments, though cutting guides 20*b*, 20*c* are sufficient for cutting and fabricating precise and effective cervical and lumbar allografts. The operation of an apparatus with cutting guides 20*a*, 20*b*, 20*c* versus the operation of an apparatus with cutting guides 20*b*, 20*c* will become clearer as this specification continues.

Depending on the allograft being fabricated, the angle of vertical cutting guides 20*a*-20*c*, horizontal cutting guides 20*a'*-20*c'*, and/or notches 21*a*-21*c* can be critical for fabricating the precise allograft needed for implantation into a human being. For example, in a cervical spinal fusion requiring a wedge to be implanted between the cervical vertebrae of a patient, at least one edge (and sometimes both edges) of the wedge needs to be angled. This angle typically is approximately five (5) degrees to fabricate a precise cervical allograft wedge. Thus, the angle of cutting guides 20*a*-20*c*, horizontal cutting guides 20*a'*-20*c'*, and/or notches 21*a*-21*c* provides an important function and structure for the particular allograft being created.

Figure 8:
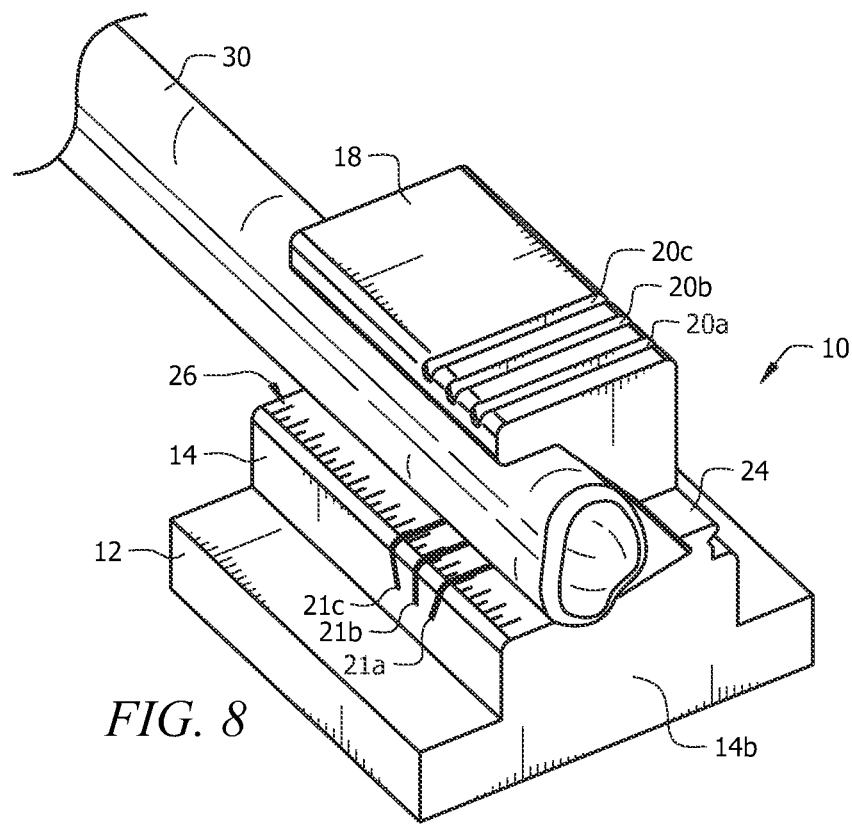
FIG. 8 depicts a cortical strut positioned to be cut and/or fabricated within an embodiment of the current invention.

FIGS. 8-9 depicts apparatus 10 in use/practice by a user, for example a surgical team. In operation for the fabrication of an allograft, a user slides graft material 30 into channel 16 in overlying relation to base 14 and within the interior spatial confines of hood 18. Graft material 30 traverses channel 16 until aligned under cutting guides 20*a*, 20*b*, 20*c*, as desired by the user, depending on the allograft being fabricated. The user makes the first cut by inserting an appropriate blade into cutting guide 20*b*. This allows any blunt or rough end of graft material 30 to be cut off and wasted or repurposed. At this point, the lead edge of graft material 30 should be square and clean. Thereafter, graft material 30 can be positioned/slid further forward or backward based on the depth needed for the allograft. The user then makes the second cut by inserting an appropriate blade into cutting guide 20*a* or 20*c*. Upon making this cut, the allograft is formed and can be pushed through second end 14*b* of channel 16 to the external environment.

In an embodiment when fabricating cervical allografts, cutting guide 20*a* or 20*c* has an approximately five (5) degree angle toward cutting guide 20*b*, such that the second cut is an angled cut to form the desired wedge or ring. In certain applications, the lead end of the allograft is substantially straight and vertical (via cutting guide 20*b*), and the trail end of the allograft is angled (via cutting guide 20*c*) toward cutting guide 20*b*. In other applications, the trail end of the allograft is substantially straight and vertical (via cutting guide 20*b*), and the lead end of the allograft is angled (via cutting guide 20*a*) toward cutting guide 20*b*. Alternatively, if the desired wedge requires sloped edges on both sides, each cut can be made via cutting guides 20*a*, 20*c*.

In other embodiments where cutting guides 20*b*, 20*c* are present, potentially without cutting guide 20*a*, the lead end of the allograft is substantially straight and vertical (via cutting guide 20*b*), and the trail end of the allograft is angled (via cutting guide 20*c*) toward cutting guide 20*b*. Alternatively, if the desired wedge requires sloped edges on both sides, both cuts can be made via cutting guide 20*c* and by rotating graft material 30 within channel 16. The user can also perform this rotation and angled cut to save graft material for use on the next allograft.

Other Optional Additions or Alterations to Apparatus 10

Fourth surface 108 of channel 16, along with other troughs, joint and surfaces (not shown), is an optional addition to channel 16 to further secure the bone or graft material within channel 16. In an embodiment, fourth surface 108 can include a supplementary crook or flexure that can slide or be otherwise added within channel 16 to secure varying types and shapes of graft materials. This supplementary crook itself can take varying shapes to adapt to specific graft material types, such as cortical struts or fibular struts. Without this supplementary crook, apparatus 10 may look similar to apparatus 10 seen in FIG. 7.

In certain embodiments, at its peak (i.e., joint 116), third surface 106 can terminate at a hinged member (not shown, or for example, fourth surface 108 can be hingedly connected to third surface 106) that is capable of opening and closing channel 16 from the front, further securing the graft material within channel 16, if needed.

Hood 18 overhangs base 14 and closes off channel 16 at least from the rear and the top of channel 16 and as such includes a rear portion and a top portion. Hood 18 helps secure the graft material within channel 16. Optionally, hood 18 can include a downwardly-extending front face (not shown) that would provide a barrier from the external environment in front of apparatus 10. However, this front face is not necessarily needed to sufficiently hold the graft material in place within channel 16. Surfaces 102-108 provide sufficient structure to hold the graft material in place, optionally with forceps 34 (FIG. 10), for cutting. Hood 18 has a longitudinal extent positioned along the entirety of the lead and trail portion of base 14. A gap may exist between hood 18 and base 14, as indicated in FIG. 7. Otherwise, hood 18 may close off channel 16 entirely from the external environment in the front.

The rear edge of hood 18 may optionally be hingedly connected to base 14 such that hood 18 can pivot up and down, for example to allow placement of the graft material prior to securing the graft material in place. However, it can be appreciated that if hood 18 is fixed to base 14, the graft material can slide in and out of channel 18.

Graft material 30 may or may not be able to slide freely within channel 16 when base 14 and hood 18 has secured graft material 30 within channel 16. As graft material 30 slides within channel 16 toward second end 14b of base 14, hood 18 may be tightened or loosened accordingly, if possible, though hood 18 may alternatively be affixed to base 14 without ability to tighten or loosen. In a typical scenario, graft material 30 slides into channel 16 at the lead portion of base 14 and slides toward the trail portion of base 14 for subsequent cutting.

The top surface of base 14 further can optionally also include one or more slide rails or channels (not shown) to which the lower surface of the upper portion of hood 18 is connected. The slide rails or channels are transversely positioned normal to the longitudinal extent of hood 18, such that hood 18 can move toward the front and toward the rear of apparatus 10.

A locking means (not shown) can be disposed on the top or other surface of hood 18. The locking means can be any structure or apparatus that locks or secures hood 18 in place, thereby securing the graft material within channel 16. Examples of locking means include, but are not limited to, a hex bolt, a snap connector, locking discs and barrel bolts, hooks, other bolts, electronically-controlled locks, pins, pop-up pins, etc.

EXAMPLE

The following example is described for illustrative purposes only and is not intended to be limiting of the scope of the current invention.

The resulting bone graft as cut by an embodiment of the current invention has the following dimensions. The diameter of the bone graft is about twelve (12) to about thirteen (13) millimeters. The graft size is about twelve (12) millimeters high and about thirteen (13) to about fourteen (14) millimeters wide. The width of the bone graft is determined by the user making the second cut using apparatus 10.

These specifications typically result in a cervical bone graft.

A larger size bone graft, and thus potentially a larger size apparatus, according to the current invention, can be utilized for lumbar bone grafts.

Optionally, certain embodiments of the current invention are a one-time use, disposable product, though in other embodiments, the current invention a sustainable, multi-use apparatus.

GLOSSARY OF CLAIM TERMS

Aligned: This term is used herein to refer to two cutting guides falling into line with each other or otherwise forming a straight line therebetween, such that when a blade is inserted into a cutting guide, the blade can follow a path of travel through a corresponding aligned cutting guide or through a corresponding aligned notch.

Angie toward cutting guide: This term is used herein to refer to an angled or tilted cutting guide pointing toward an adjacent cutting guide.

Blade: This term is used herein to refer to any medical tool or instrument that can be used to cut through graft material, such as cortical struts, for fabrication of allografts.

Channel: This term is used herein to refer to a specifically-shaped passageway that fits the graft material intended to be cut and fabricated into allografts.

Entry end: This term is used herein to refer to the end of the lead portion of the base where the graft material enters the channel.

Excessive spatial leeway: This term is used herein to refer to a degree of freedom of a blade to shift or move about while cutting the graft material within the channel of the current invention. For example, if a blade is given too much room to move irregularly, particularly side to side, then the accuracy of the cut may be compromised. Cutting guides are thus thin to prevent this from occurring.

Exit end: This term is used herein to refer to the end of the trail portion of the base where the graft material (and possibly resulting allografts) exit the channel.

Front interruption: This term is used herein to refer to a generally solid component formed in the hood between a vertical cutting guide and a corresponding aligned horizontal cutting guide in proximity to the rear of the apparatus, where the rear interruption does not permit a blade or other apparatus to slide therethrough.

Gap: This term is used herein to refer to an opening between the front portion of the hood and the base thereunder along the front of the apparatus.

Hood: This term is used herein to refer to a component that helps secure a graft material within the channel of the current invention. The hood typically forms a rear barrier and a top barrier of the channel. The hood helps minimize any transverse movement of the graft material within the channel.

Horizontal cutting guide: This term is used herein to refer to thin slits within the rear portion of the hood through which the external environment to the rear of the apparatus is in open communication with the interior of the channel. The horizontal cutting guide is adapted to receive an appropriate blade for cutting the graft material.

Irregular shape: This term is used herein to refer to the channel's variable shape or form that is defined by the graft material that would be inserted into and cut within the channel. Because of the shape of different graft materials (e.g., cortical struts), typically the "irregular shape" would not be circular, ovular, square, rectangular, or other standard shape.

Joint: This term is used herein to refer to a connection point between two planes.

Lead portion: This term is used herein to refer to the initial segment of the base into which the graft material enters the apparatus.

Notch: This term is used herein to refer to an indentation or a thin slit in a top surface of the base, such that when the blade cuts through the graft material through a cutting guide, the blade can follow through the graft material into a corresponding aligned notch.

Predetermined angle: This term is used herein to refer to a tilt relative to a vertical axis of the current invention. Thus, angles are provided herein relative to this vertical axis, including an angle capable of being completely vertical (i.e., overlapping the vertical axis).

Rear interruption: This term is used herein to refer to a generally solid component formed in the hood between a vertical cutting guide and a corresponding aligned horizontal cutting guide in proximity to the rear of the apparatus, where the rear interruption does not permit a blade or other apparatus to slide therethrough.

Shape of allograft: This term is used herein to refer to the outer physical contour or configuration of an allograft desired upon use of the current invention.

Support flange: This terra is used herein to refer to an extension from the base of the apparatus, where the support flange is used to support or balance the apparatus during use.

Trail portion: This term is used herein to refer to the segment of the base where the cutting area and cutting guides are located. The trail portion also is the subsequent segment into which the graft material is slid from the lead portion.

Vertical cutting guide: This term is used herein to refer to thin slits within the top portion of the hood through which the external environment above the apparatus is in open communication with the interior of the channel. The vertical cutting guide is adapted to receive an appropriate blade for cutting the graft material.

Vertically-oriented: This term is used herein to refer to an angle of a cutting guide that would overlap the vertical axis of the apparatus.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An apparatus for cutting a graft material and fabricating an allograft from said graft material, comprising:
    a base defining a front of said apparatus, a rear of said apparatus, a left side of said apparatus, a right side of said apparatus, a top of said apparatus, and a bottom of said apparatus,
    said base having a lead portion and a trail portion, said lead portion have an entry end, said trail portion have an exit end, said entry end and said exit end having substantially the same size and shape;
    a hood coupled to said base and positioned in overlying relation to said base, said hood having a top portion, a front portion, and a rear portion;
    a channel disposed between said base and said hood, said channel disposed in overlying relation to said base and in underlying relation to said hood, said channel having an irregular shape to secure said graft material therewithin, said channel having a first end in communication with said entry end of said base, said channel further having a second end in communication with said exit end of said base,
    said channel being spatially confined on a bottom side, a top side, and a rear side by said base and said hood;
    a first vertical cutting guide disposed through said top portion of said hood in proximity to said second end of said hood, said first vertical cutting guide providing open communication between said top of said apparatus and an interior of said channel through said first vertical cutting guide, said first vertical cutting guide structured to receive a blade without excessive spatial leeway such that said blade is capable of accurately cutting said graft material from said top of said apparatus through said first vertical cutting guide, said first vertical cutting guide being disposed at a first predetermined angle based on a shape of said allograft needed; and
    a second vertical cutting guide disposed through said top portion of said hood adjacent to said first vertical cutting guide, said second vertical cutting guide providing open communication between said top of said apparatus and said interior of said channel through said second vertical cutting guide, said second vertical cutting guide structured to receive said blade without excessive spatial leeway such that said blade is capable of accurately cutting said graft material from said top of said apparatus through said second vertical cutting guide, said second vertical cutting guide being disposed at a second predetermined angle based on said shape of said allograft needed.

2. An apparatus as in claim 1, further comprising:
    a first horizontal cutting guide disposed through said rear portion of said hood in proximity to said second end of said hood, said first horizontal cutting guide providing open communication between said rear of said apparatus and said interior of said channel through said first horizontal cutting guide, said first horizontal cutting guide structured to receive said blade without excessive spatial leeway such that said blade is capable of accurately cutting said graft material from said front or rear of said apparatus through said first horizontal cutting guide, said first horizontal cutting guide being aligned with said first vertical cutting guide, said first horizontal cutting guide being disposed at said first predetermined angle; and
    a second horizontal cutting guide disposed through said rear portion of said hood adjacent to said first horizontal cutting guide, said second horizontal cutting guide providing open communication between said rear of said apparatus and said interior of said channel through said second horizontal cutting guide, said second horizontal cutting guide structured to receive said blade without excessive spatial leeway such that said blade is capable of accurately cutting said graft material from said front or rear of said apparatus through said second horizontal cutting guide, said second horizontal cutting guide being aligned with said second vertical cutting guide, said second horizontal cutting guide being disposed at said second predetermined angle.

3. An apparatus as in claim 2, further comprising:
    a first rear interruption between said first vertical cutting guide and said first horizontal cutting guide, such that said blade is incapable of passing from said first vertical cutting guide to said first horizontal cutting guide through said first rear interruption; and
    a second rear interruption between said second vertical cutting guide and said second horizontal cutting guide, such that said blade is incapable of passing from said second vertical cutting guide to said second horizontal cutting guide through said second rear interruption.

4. An apparatus as in claim 1, further comprising:
    a first front interruption disposed in said front portion of said hood in said first vertical cutting guide, such that said first vertical cutting guide is not in open communication with said front of said apparatus; and
    a second front interruption disposed in said front portion of said hood in said second vertical cutting guide, such that said second vertical cutting guide is not in open communication with said front of said apparatus.

5. An apparatus as in claim 1, further comprising:
said first predetermined angle being a range between about three (3) degrees and about six (6) degrees toward said second vertical cutting guide, and
said second predetermined angle being vertically-oriented.

6. An apparatus as in claim 5, further comprising:
said first predetermined angle being about (5) degrees.

7. An apparatus as in claim 1, further comprising:
a first notch in said base that is aligned with said first vertical cutting guide, said first notch being disposed at said first predetermined angle; and
a second notch in said base that is aligned with said second vertical cutting guide, said second notch being disposed at said second predetermined angle.

8. An apparatus as in claim 1, further comprising:
a third vertical cutting guide disposed through said top portion of said hood adjacent to said first and second vertical cutting guides on an opposite side of said second vertical cutting guide from said first vertical cutting guide, said third vertical cutting guide providing open communication between said top of said apparatus and said interior of said channel through said third vertical cutting guide, said third vertical cutting guide structured to receive said blade without excessive spatial leeway such that said blade is capable of accurately cutting said graft material from said top of said apparatus through said third vertical cutting guide, said third vertical cutting guide being disposed at a third predetermined angle based on said shape of said allograft needed.

9. An apparatus as in claim 8, further comprising:
a first horizontal cutting guide disposed through said rear portion of said hood in proximity to said second end of said hood, said first horizontal cutting guide providing open communication between said rear of said apparatus and said interior of said channel through said first horizontal cutting guide, said first horizontal cutting guide structured to receive said blade without excessive spatial leeway such that said blade is capable of accurately cutting said graft material from said front or rear of said apparatus through said first horizontal cutting guide, said first horizontal cutting guide being aligned with said first vertical cutting guide, said first horizontal cutting guide being disposed at said first predetermined angle;
a second horizontal cutting guide disposed through said rear portion of said hood adjacent to said first horizontal cutting guide, said second horizontal cutting guide providing open communication between said rear of said apparatus and said interior of said channel through said second horizontal cutting guide, said second horizontal cutting guide structured to receive said blade without excessive spatial leeway such that said blade is capable of accurately cutting said graft material from said front or rear of said apparatus through said second horizontal cutting guide, said second horizontal cutting guide being aligned with said second vertical cutting guide, said second horizontal cutting guide being disposed at said second predetermined angle; and
a third horizontal cutting guide disposed through said rear portion of said hood adjacent to said first and second horizontal cutting guides, said third horizontal cutting guide providing open communication between said rear of said apparatus and said interior of said channel through said third horizontal cutting guide, said third horizontal cutting guide structured to receive said blade without excessive spatial leeway such that said blade is capable of accurately cutting said graft material from said front or rear of said apparatus through said third horizontal cutting guide, said third horizontal cutting guide being aligned with said third vertical cutting guide, said third horizontal cutting guide being disposed at said third predetermined angle.

10. An apparatus as in claim 9, further comprising:
a first rear interruption between said first vertical cutting guide and said first horizontal cutting guide, such that said blade is incapable of passing from said first vertical cutting guide to said first horizontal cutting guide through said first rear interruption;
a second rear interruption between said second vertical cutting guide and said second horizontal cutting guide, such that said blade is incapable of passing from said second vertical cutting guide to said second horizontal cutting guide through said second rear interruption; and
a third rear interruption between said third vertical cutting guide and said third horizontal cutting guide, such that said blade is incapable of passing from said third vertical cutting guide to said third horizontal cutting guide through said third rear interruption.

11. An apparatus as in claim 8, further comprising:
a first front interruption disposed in said front portion of said hood in said first vertical cutting guide, such that said first vertical cutting guide is not in open communication with said front of said apparatus;
a second front interruption disposed in said front portion of said hood in said second vertical cutting guide, such that said second vertical cutting guide is not in open communication with said front of said apparatus; and
a third front interruption disposed in said front portion of said hood in said third vertical cutting guide, such that said third vertical cutting guide is not in open communication with said front of said apparatus.

12. An apparatus as in claim 8, further comprising:
said first predetermined angle being a range between about three (3) degrees and about six (6) degrees toward said second vertical cutting guide,
said second predetermined angle being vertically-oriented, and
said third predetermined angle being a range between about three (3) degrees and about six (6) degrees toward said second vertical cutting guide.

13. An apparatus as in claim 12, further comprising:
said first predetermined angle and said third predetermined angle each being about five (5) degrees.

14. An apparatus as in claim 8, further comprising:
a first notch in said base that is aligned with said first vertical cutting guide, said first notch being disposed at said first predetermined angle;
a second notch in said base that is aligned with said second vertical cutting guide, said second notch being disposed at said second predetermined angle; and
a third notch in said base that is aligned with said third vertical cutting guide, said third notch being disposed at said third predetermined angle.

15. An apparatus as in claim 1, further comprising:
said base including support flanges extending to said front of said apparatus and to said rear of said apparatus.

16. An apparatus as in claim 1, further comprising:
a gap disposed between said hood and said base along said front of said apparatus, such that said interior of said channel is in open communication with said front of said apparatus.

17. An apparatus as ifs claim 1, wherein said irregular shape of said channel comprises:

a first surface that is substantially horizontal and forms said bottom side of said channel;

a second surface extending rearwardly and upwardly from said first surface;

a first joint that connects said first surface and said second surface;

a third surface extending frontwardly and upwardly from said second surface; and a second joint that connects said second surface and said third surface.

18. An apparatus as in claim 17, wherein said irregular shape of said channel further comprises:

a fourth surface that is substantially horizontal and extends frontwardly from said third surface, said fourth surface being disposed parallel to and in overlying relation to said first surface, said fourth surface forming said top side of said channel; and a third joint that connects said third surface to said fourth surface.

19. An apparatus for cutting a graft material and fabricating an allograft from said graft material, comprising:

a base defining a front of said apparatus, a rear of said apparatus, a left side of said apparatus, a right side of said apparatus, a top of said apparatus, and a bottom of said apparatus, said base having a lead portion and a trail portion, said lead portion have an entry end, said trail portion have an exit end, said entry end and said exit end having substantially the same size and shape;

a hood coupled to said base and positioned in overlying relation to said base, said hood having a top portion, a front portion, and a rear portion;

a channel disposed between said base and said hood, said channel disposed in overlying relation to said base and in underlying relation to said hood, said channel having an irregular shape to secure said graft material therewithin, said channel having a first end in communication with said entry end of said base, said channel further having a second end in communication with said exit end of said base, said channel being spatially confined on a bottom side, a top side, and a rear side by said base and said hood; and a first horizontal cutting guide disposed through said rear portion of said hood in proximity to said second end of said hood, said first horizontal cutting guide providing open communication between said rear of said apparatus and an interior of said channel through said first horizontal cutting guide, said first horizontal cutting guide structured to receive a blade without excessive spatial leeway such that said blade is capable of accurately cutting said graft material from said front or rear of said apparatus through said first horizontal cutting guide, said first vertical cutting guide being disposed at a first predetermined angle based on a shape of said allograft needed; and a second horizontal cutting guide disposed through said rear portion of said hood adjacent to said first horizontal cutting guide, said second horizontal cutting guide providing open communication between said rear of said apparatus and said interior of said channel through said second horizontal cutting guide, said second horizontal cutting guide structured to receive said blade without excessive spatial leeway such that said blade is capable of accurately cutting said graft material from said front or rear of said apparatus through said second horizontal cutting guide, said second vertical cutting guide being disposed at a second predetermined angle based on said shape of said allograft needed.

20. An apparatus for cutting a cortical strut and fabricating a cervical or lumbar allograft from said cortical strut, comprising:

a base defining a front of said apparatus, a rear of said apparatus, a left side of said apparatus, a right side of said apparatus, a top of said apparatus, and a bottom of said apparatus, said base having a lead portion and a trail portion, said lead portion have an entry end, said trail portion have an exit end, said entry end and said exit end having substantially the same size and shape, said base including support flanges extending to said front of said apparatus and to said rear of said apparatus;

a hood coupled to said base and positioned in overlying relation to said base, said hood having a top portion, a front portion, and a rear portion;

a channel disposed between said base and said hood, said channel disposed in overlying relation to said base and in underlying relation to said hood, said channel having an irregular shape to secure said graft material therewithin, said channel having a first end in communication with said entry end of said base, said channel further having a second end in communication with said exit end of said base, said channel being spatially confined on a bottom side by said base, a top side by said hood, and a rear side by said hood, wherein said irregular shape of said channel includes:

a first surface that is substantially horizontal and forms said bottom side of said channel, a second surface extending rearwardly and upwardly from said first surface, a first joint that connects said first surface and said second surface, a third surface extending frontwardly and upwardly from said second surface, a second joint that connects said second surface and said third surface, a fourth surface that is substantially horizontal and extends frontwardly from said third surface, said fourth surface being disposed parallel to and in overlying relation to said first surface, and a third joint that connects said third surface to said fourth surface;

a gap disposed between said hood and said base along said front of said apparatus, such that said interior of said channel is in open communication with said front of said apparatus;

a first vertical cutting guide disposed through said top portion of said hood in proximity to said second end of said hood, said first vertical cutting guide providing open communication between said top of said apparatus and an interior of said channel through said first vertical cutting guide, said first vertical cutting guide structured to receive a blade without excessive spatial leeway such that said blade is capable of accurately cutting said graft material from said top of said apparatus through said first vertical cutting guide, said first vertical cutting guide being disposed at a first predetermined angle based on a shape of said allograft needed;

a second vertical cutting guide disposed through said top portion of said hood adjacent to said first vertical cutting guide, said second vertical cutting guide providing open communication between said top of said apparatus and said interior of said channel through said second vertical cutting guide, said second vertical cutting guide structured to receive said blade without excessive spatial leeway such that said blade is capable of accurately cutting said graft material from said top of said apparatus through said second vertical cutting guide, said second vertical cutting guide being disposed at a second predetermined angle based on said shape of said allograft needed, said second predetermined angle being vertically-oriented, said first predetermined angle being about five (5) degrees toward said second vertical cutting guide;

a third vertical cutting guide disposed through said top portion of said hood adjacent to said first and second vertical cutting on an opposite side of said second vertical cutting guide from said first vertical cutting guide, said third vertical cutting guide providing open communication between said top of said apparatus and said interior of said channel through said third vertical cutting guide, said third vertical cutting guide structured to receive said blade without excessive spatial leeway such that said blade is capable of accurately cutting said graft material from said top of said apparatus through said third vertical cutting guide, said third vertical cutting guide being disposed at a third predetermined angle based on said shape of said allograft needed, said third predetermined angle being about five (5) degrees toward said second vertical cutting guide;

a first horizontal cutting guide disposed through said rear portion of said hood in proximity to said second end of said hood, said first horizontal cutting guide providing open communication between said rear of said apparatus and said interior of said channel through said first horizontal cutting guide, said first horizontal cutting guide structured to receive said blade without excessive spatial leeway such that said blade is capable of accurately cutting said graft material from said front or rear of said apparatus through said first horizontal cutting guide, said first horizontal cutting guide being aligned with said first vertical cutting guide, said first horizontal cutting guide being disposed at said first predetermined angle;

a second horizontal cutting guide disposed through said rear portion of said hood adjacent to said first horizontal cutting guide, said second horizontal cutting guide providing open communication between said rear of said apparatus and said interior of said channel through said second horizontal cutting guide, said second horizontal cutting guide structured to receive said blade without excessive spatial leeway such that said blade is capable of accurately cutting said graft material from said front or rear of said apparatus through said second horizontal cutting guide, said second horizontal cutting guide being aligned with said second vertical cutting guide, said second horizontal cutting guide being disposed at said second predetermined angle;

a third horizontal cutting guide disposed through said rear portion of said hood adjacent to said first and second horizontal cutting guides, said third horizontal cutting guide providing open communication between said rear of said apparatus and said interior of said channel through said third horizontal cutting guide, said third horizontal cutting guide structured to receive said blade without excessive spatial leeway such that said blade is capable of accurately cutting said graft material from said front or rear of said apparatus through said third horizontal cutting guide, said third horizontal cutting guide being aligned said third vertical cutting guide, said third horizontal cutting guide being disposed at said third predetermined angle;

a first rear interruption between said first vertical cutting guide and said first horizontal cutting guide, such that said blade is incapable of passing from said first vertical cutting guide to said first horizontal cutting guide through said first rear interruption;

a second rear interruption between said second vertical cutting guide and said second horizontal cutting guide, such that said blade is incapable of passing from said second vertical cutting guide to said second horizontal cutting guide through said second rear interruption;

a third rear interruption between said third vertical cutting guide and said third horizontal cutting guide, such that said blade is incapable of passing from said third vertical cutting guide to said third horizontal cutting guide through said third rear interruption;

a first front interruption disposed in said front portion of said hood in said first vertical cutting guide, such that said first vertical cutting guide is not in open communication with said front of said apparatus;

a second front interruption disposed in said front portion of said hood in said second vertical cutting guide, such that said second vertical cutting guide is not in open communication with said front of said apparatus; and a third front interruption disposed in said front portion of said hood in said third vertical cutting guide, such that said third vertical cutting guide is not in open communication with said front of said apparatus;

a first notch in said base that is aligned with said first vertical cutting guide, said first notch being disposed at said first predetermined angle;

a second notch in said base that is aligned with said second vertical cutting guide, said second notch being disposed at said second predetermined angle; and a third notch in said base that is aligned with said third vertical cutting guide, said third notch being disposed at said third predetermined angle.

* * * * *

UNITED STATES PATENT AND TRADEMARK OFFICE
CERTIFICATE OF CORRECTION

PATENT NO.        : 8,800,158 B1
APPLICATION NO.   : 14/254430
DATED             : August 12, 2014
INVENTOR(S)       : John H. Shim Page 1 of 1

It is certified that error appears in the above-identified patent and that said Letters Patent is hereby corrected as shown below:

In the Claims

Column 16, Claim 17, Line 66 should read: An apparatus as in claim 1, wherein said irregular Signed and Sealed this
Twenty-first Day of October, 2014

Michelle K. Lee
*Deputy Director of the United States Patent and Trademark Office*